United States Patent [19]

Papa et al.

[11] Patent Number: 4,535,187

[45] Date of Patent: Aug. 13, 1985

[54] PREPARATION OF ISOPHORONE AND MESITYL OXIDE FROM ACETONE

[75] Inventors: Anthony J. Papa, St. Albans; Steven W. Kaiser, South Charleston, both of W. Va.

[73] Assignee: Union Carbide Corporation, Danbury, Conn.

[21] Appl. No.: 564,023

[22] Filed: Dec. 21, 1983

[51] Int. Cl.³ .............................................. C07C 45/45
[52] U.S. Cl. .................................. 568/353; 568/388; 568/716; 502/341
[58] Field of Search ................ 568/343, 388, 353, 716

[56] References Cited

U.S. PATENT DOCUMENTS

| | | | |
|---|---|---|---|
| 2,183,127 | 12/1930 | Vaughan et al. | 260/586 |
| 2,393,510 | 1/1946 | Bailey, Jr. et al. | 260/586 |
| 2,419,142 | 4/1947 | Ipatieff et al. | 260/668 |
| 2,425,096 | 8/1947 | Ipatieff et al. | 260/668 |
| 2,429,361 | 10/1947 | Linn et al. | 260/586 |
| 2,451,350 | 10/1948 | Mottern et al. | 260/586 |
| 2,549,508 | 4/1951 | Mottern | 260/586 |
| 3,410,909 | 11/1968 | Fleischer et al. | 260/593 |
| 4,086,188 | 4/1978 | Reichle | 252/463 |
| 4,165,339 | 8/1979 | Reichle | 260/586 |

FOREIGN PATENT DOCUMENTS

| | | |
|---|---|---|
| 909941 | 11/1962 | United Kingdom . |
| 921510 | 3/1963 | United Kingdom . |
| 1010695 | 11/1965 | United Kingdom . |

OTHER PUBLICATIONS

Archiv der Pharmazie, 406, 305 (6), (1972).

*Primary Examiner*—James H. Reamer
*Attorney, Agent, or Firm*—Bernard Francis Crowe

[57] ABSTRACT

The aldol condensation of acetone to isophorone and mesityl oxides in high conversions and efficiencies is achieved by a catalyst comprising a calcined calcium salt deposited on an alumina support.

5 Claims, No Drawings

PREPARATION OF ISOPHORONE AND MESITYL OXIDE FROM ACETONE

BACKGROUND OF THE INVENTION

This invention pertains to the aldol condensation of acetone to produce isophorone and mesityl oxide. More particularly, this invention pertains to the use of a catalyst for the aforesaid purpose prepared by the deposition of a calcium salt on particular alumina supports followed by calcination.

The gas phase aldol condensation of acetone at high temperatures to give a variety of products including mesityl oxide, isophorone, mesitylene, phorone, and 3,5-xylenol is well known in the art. The processes are complicated by the inability to obtain a single product and especially the presence of numerous low value high boiling materials.

Numerous conventional, strongly basic heterogeneous catalysts such as magnesium and calcium hydroxide are known. For example, U.S. Pat. No. 2,183,127 describes the vapor phase condensation of acetone in the presence of CaO or $Ca(OH)_2$ catalyst at 350° C. to 400° C. to give isophorone in 25% yield, U.S. Pat. No. 2,393,510 claims the vapor phase condensation of acetone over sodium or calcium aluminate at 424° C. and a liquid hourly space velocity of 0.35 hr.$^{-1}$ to get 15% acetone conversion and a yield of about 43% isophorone, 32% mesityl oxide and 25% higher boiling products. The use of other bulk oxide and mixed oxide catalysts are described in several references for the condensation of acetone to isophorone, viz., U.S. Pat. No. 4,086,188; U.S. Pat. No. 4,165,339; U.S. Pat. No. 2,549,508; British Pat. No. 909,941; British Pat. No. 1,010,695 and U.S. Pat. No. 2,451,350. Only a few disclosures have been made for the use of $Al_2O_3$ or metal oxide(s) supported on $Al_2O_3$. These include U.S. Pat. No. 2,429,361; U.S. Pat. No. 2,425,096; U.S. Pat. No. 2,419,142 and H. J. Seebald et al. Archive der Pharmazie, 406, 305(6) (1972). However, the efficencies to a desired product, e.g., isophorone achievable by this process are barely satisfactory and far less satisfactory in respect to the acetone conversion achieved per pass. Also, the above heterogeneous catalyst when employed as vapor phase catalysts either require high temperature (350° to 400° C.), are of short life and/or tend to be fragile which provides a more expensive process. The co-precipitated mixed oxide catalysts have the drawback of exhibiting poor catalyst manufacturing reproducibility and are expensive.

It is, therefore, an object of this invention to provide long life, regenerable solid catalysts for the process of aldolization of acetone to yield chiefly isophorone and mesityl oxide.

It is a further object that the aforesaid catalyst operate in an heterogeneous system.

It is still another object that the process lend itself to the aldolization and dehydration of acetone in the vapor phase over a fixed catalyst bed.

It is still a further object of this invention that isophorone and mesityl oxide are produced in high conversion per pass.

It is another object of this invention that the catalyst used can be manufactured reproducibly and economically.

Other objects will become apparent to those skilled in the art upon a further reading of the specification.

SUMMARY OF THE INVENTION

The above objects are met by preparing a catalyst by a process which comprises:

(a) Introducing onto an alumina support a sufficient amount of an inorganic or organic calcium salt to provide a loading of from about 1 to about 20 weight percent of calcium in the final catalyst whereby the alumina has a surface area in excess to about 30 meters$^2$/gram and an average pore volume in excess of about 0.40 cc/gram; and (b) calcining the alumina supported calcium salt from step (a) at a temperature of about 300° to about 600° C. for at least about 3 hours.

The nature of the anions used in the calcium salts is not critical. Thus, for example, organic salts, such as Ca salts of aliphatic acids, including acetic acid, propionic acid, isobutyric acid, valeric acid, hexanoic acids, and the like, can be used as well as phenolates including Ca salts of monophenols such as phenol, p-tert-butyl phenol, 2,4,6-trimethyl phenol, and the like. Salts containing inorganic anions are equally useful, such as nitrates, sulfates, phosphates, and the like.

The preferred salt is calcium acetate.

The amount of calcium, calculated as calcium metal, remaining deposited on the alumina after calcining can vary from about 1% by weight to about 20% by weight. It is preferred to have about 3 to about 10% by weight of calcium and even more preferred, 7 to about 10 weight percent.

The form of the calcium in the final supported catalyst is not completely understood. The calcium may be present as an oxide, a carbonate, an aluminate or some other form, existing as either discrete particles on the surface or intimately bound to the support surface.

The physical nature of the alumina support is critical. They should be characterized by high surface area and high pore volume. Surface areas in excess of about 30 meters$^2$/gram and pore volumes in excess of about 0.40 cc/gram are preferred.

The physical form of the alumina is not critical and can be in the form of tablets, granules, spheres, and extrudates preferably having diameters of about 2 to about 20 mm and lengths of about 2 to about 50 mm. The alumina supported catalyst may be crushed to suitable size and packed to form a solid.

The method of introducing the calcium salt onto the alumina support is critical for obtaining maximum catalytic activity. Impregnation and incipient wetness techniques are preferred. The former consists of soaking the alumina in aqueous solutions of the calcium salts enumerated above followed by drying of the soaked supports.

The incipient wetness technique consists of just filling the pore volume of the support with an equivalent amount of salt solution under vacuum and drying. In contrast, co-forming the alumina and the calcium simultaneously results in a catalyst generally of significantly lower activity. This is probably due to the fact that much of the calcium is *not on the support surface* and thus is not accessible for catalytic activity.

The aldolization process is carried out by passing acetone vapor over a fixed bed of the solid catalyst at elevated temperature. The preferred temperature of aldolization is about 275° C. to about 350° C. with temperatures of about 290° C. to about 310° C. being more preferred. At temperatures below about 275° C. the reaction takes place but is too slow to be commercially feasible. At temperatures greater than about 350° C. the yield loss due to side reactions becomes excessive.

The pressure is preferably atmospheric or slightly above atmospheric pressure. The preferred pressures are about 1 to about 200 atmospheres although pressures of about 1 to about 10 atmospheres are more preferred for simplification of the commercial process.

The condensed liquids and gaseous products are collected and analyzed with equipment and techniques known to those skilled in the art. Liquid acetone feed is passed through a preheater vaporization zone of a tubular reactor at a rate of about one volume of feed per volume of catalyst per hour.

An unexpected advantage of the catalyst used in this invention is the reproducibility of yield and conversion of acetone to isophorone and mesityl oxide.

The invention is further described in the examples which follow. All parts and percentages are by weight unless otherwise specified.

EXPERIMENTAL

A. Calculations $$\text{Conversion (\%)} = \frac{\text{Equivalents of Acetone Consumed}}{\text{Equivalents of Acetone Fed}} \times 100$$

$$\text{Efficiency (\%)} = \frac{\text{Equivalents of Acetone in the Isophorone and Mesityl Oxide Recovered}}{\text{Equivalents of Acetone consumed}} \times 100$$

B. Catalyst Preparation

The alumina support is soaked for about one hour at 25° C. in a 20% solution of calcium acetate in water. After draining off excess calcium acetate solution, the soaked catalyst is dried with warm air at 400° C. for three hours. The process is repeated until the calcined catalyst contains the desired concentration of calcium.

The characterization of the alumina supports used in this invention are delineated in Table IV.

C. Examples 1-5

Fourteen grams of impregnated catalyst, which had been screened to 14–20 mesh, was placed in a 0.50 inch by 36 inch glass tube and covered with five inches of glass beads. The weight of catalyst generally gave an eight-inch bed length. The tube was constructed to allow nitrogen and acetone to be fed to the top at atmospheric pressure. The liquid products were collected in a tank at the base and gaseous products vented to a dry ice trap. The tube was heated by an electric furnace (through aluminum foil) and monitored through three thermocouples placed along the catalyst bed. Before feeding acetone the catalyst was conditioned for 20 hours at 350° C. in the pressure of air (flow rate=2 liters/hour). Acetone (92.4% acetone, 4.3% water, 2.0% mesityl oxide, and 1.3% other products) was fed on top of the heated glass beads at a rate of 18 ml/hr and the temperature maintained at 300° C. The liquid and gaseous products were condensed and analyzed by gas chromatography and the results given in Table I. Only the data relative to isophorone and mesityl oxide are reported here. The other products are miscellaneous high boilers and about 0.1 to about 0.5 weight percent of 3,5-xylenol.

The results of the table clearly show the high activity of a calcium impregnated alumina and that co-formed calcium-alumina compositions are significantly less active catalysts.

After 1080 hours, the catalyst of Example 2 was regenerated by heating for 68 hours at 350° C. in a stream of air (2 liters/hr) and tested for 600 hours. The results, given in Example 4 (Table I), show that the activity was restored.

D. Examples 6-11

In this example 20 grams of the impregnated catalyst ground and screened at 8–10 mesh was placed in a tubular reactor having an inner diameter of 25 mm and a total length of 48 cm and covered with six inches of glass beads. The catalyst bed corresponded to about 50 mm in length. Pure acetone from Matheson Coleman and Bell (catalog #AX0115, assay 99.6%, H$_2$O 0.4%) was fed to the conditioned catalyst at a rate of 22 ml/hour. One hour samples were taken periodically and analyzed. Results are shown in Table II.

As can be seen from this Table, the yield of isophorone is a function of the alumina support used as well as the level of calcium contained on the support.

E. Examples 12-21

Six inches (19.3 ml) of catalyst (14–20 mesh) was placed in the reactor used in Example 1 as well as the conditions employed in Example 1 except that acetone was fed at a rate of 18 ml/hr and the acetone composition was (88.0% acetone, 6.4% water, 2.2% mesityl oxide, and 3.4% others). These examples again show in Table III the importance of employing particular Al$_2$O$_3$ supports, high concentration of calcium and impregnated extrudates.

TABLE I

|  | Example | | | | |
|---|---|---|---|---|---|
|  | 1 | 2 | 3 | 4 | 5 |
|  | Catalyst Support | | | | |
|  | A | A | B | A | A |
|  | Impregnated Extrudates | | | | Co-Formed |
| Preparative Method | (Norton SA 6176) | (Norton SA 6176) | (Kaiser KA-201) | (Reactivated SA 6176) | (Norton SA 6176) |
| Calcium, wt. % | 7.9 | 7.9 | 8.2 | 7.9 | 7.3 |
| Hours on Steam | 600 | 1080 | 504 | 600 | 312 |
| Isophorone, wt. % | 9.6 | 8.0 | 9.6 | 8.6 | 4.8 |
| Mesityl Oxide, wt. | 5.4 | 5.7 | 5.6 | 5.7 | 5.4 |
| Conversion, % | 24.1 | 21.5 | 24.3 | 22.6 | 15.9 |
| Efficiency, % | 80.3 | 82.7 | 80.6 | 81.9 | 82.4 |

TABLE II

| | Example | | | | | |
|---|---|---|---|---|---|---|
| | 6 | 7 | 8 | 9 | 10 | 11 |
| Catalyst Support | C (Calsicat Type I) | C (Calsicat Type I) | D (Alcoa F-1) | E (Alcoa H-151) | E (Alcoa H-151) | B (Kaiser KA-201) |
| Calcium, wt. % | 3.4 | 5.5 | 6.8 | 4.0 | 8.0 | 4.0 |
| Hours on Steam | 1200 | 1270 | 97 | 116 | 70 | 744 |
| Isophorone, wt. % | 2.7 | 4.7 | 1.5 | 1.7 | 1.6 | 1.8 |
| Mesityl Oxide, wt. | 8.4 | 7.9 | 5.4 | 7.0 | 7.0 | 8.5 |
| Conversion, % | 18 | 20 | 11 | 12 | 19 | 19 |
| Efficiency, % | 72 | 74 | 80 | 90 | 51 | 91 |

TABLE III

| | Example | | | | | | | | | |
|---|---|---|---|---|---|---|---|---|---|---|
| | 12 | 13 | 14 | 15 | 16 | 17 | 18 | 19 | 20 | 21 |
| Catalyst Support | A | A | A | F | G | G | H | A | B | B |
| | Impregnated Extrudates[1] | | | | | | | Co-Formed[2] | | |
| Preparative Method | (Norton SA 6176) | (Norton SA 6176) | (Norton SA 6176) | (Norton SA 6176) | (Norton SA 6173) | (Norton SA 6173) | Norton Alumina | (Norton SA 6176) | (Kaiser SA) | (Kaiser SA) |
| Calcium, wt. % | 9.1 | 9.1 | 5.6 | 5.7 | 5.7 | 5.7 | 9.5 | 9.5 | 10.4 | 12.9 |
| Hours on Steam | 576 | 836 | 168 | 168 | 168 | 574 | 48 | 48 | 528 | 528 |
| Isophorone, wt. % | 7.8 | 7.6 | 3.4 | 3.4 | 5.6 | 4.3 | 0.06 | 3.1 | 3.5 | 3.6 |
| Mesityl Oxide, wt. % | 5.4 | 5.2 | 5.3 | 5.0 | 5.0 | 4.8 | 1.7 | 4.4 | 5.1 | 5.4 |
| Conversion, % | 23.2 | 21.1 | 14.0 | 13.5 | 17.8 | 14.5 | — | 13.1 | 13.8 | 14.3 |
| Efficiency, % | 74.9 | 80.2 | 91.5 | 82.2 | 78.9 | 83.4 | — | 75.3 | 18.4 | 81.6 |

[1]External alumina which is then impregnated with aqueous calcium acetate solution.
[2]Co-formed catalysts are formed by mixing calcium acetate with $Al_2O_3$ dough and extruded.

TABLE IV

ALUMINA CHARACTERISTICS

| Catalyst Support | Acidity, μeq./g (a) | SA,[1] $M^2/g$ | PV,[2] cc/g | Mean Pore Dia. (by Vol.), microns | Mean Pore Dia. (by Area), microns | Pore Dia., Ave., microns | Micro Pores, % (b) | Macro Pores, % (b) | Bulk Density g/cc |
|---|---|---|---|---|---|---|---|---|---|
| Alcoa F-1 (D) | 50.9 | 280 | 0.173 | 21,680 | 61 | 350 | Continuous | | 1.548 |
| Alcoa H-151 (E) | 61.8 | 344 | 0.345 | 52 | 40 | 59 | 100 | 10 | 1.269 |
| Clasicat Type I (C) | — | 237 | 0.648 | 66 | 64 | 70 | 100 | 0 | 0.985 |
| Kaiser KA 201 (B) | — | 298 | 0.312 | 79 | 43 | 80 | 70 | 30 | 1.259 |
| Norton SA 6173 (G) | 87.8 | 101 | 0.479 | 64 | 64 | 70 | 97 | 3 | 1.170 |
| Norton SA 6176 (A) | 93 | 275 | 0.843 | 136 | 65 | 122 | 67 | 33 | 0.824 |
| Norton SA 6175 (F) | — | 198 | 0.41 | — | — | — | — | — | — |
| Norton (H) | 1 | 3.5 | 0.235 | — | — | — | — | — | — |

(a) Total acidity determined by adsorption of pyridine.
(b) Micro pores = volume % with < 200 pore diameter; and Macro pores = volume % with > 200 pore diameter.
[1]Surface area.
[2]Pore volume.

While the primary purpose of this invention is to convert acetone to isophorone and mesityl oxide, there is some by-product formation. Some of these by-products are useful in their own right. Thus, for example, if one also wanted to convert acetone to 3,5-xylenol, use of a reation temperature of about 370° to about 450° C. at a space velocity of 0.25 to 1.0 hours$^{-1}$ in the process of this invention will achieve that end.

Although the invention has been described in its preferred forms with a certain degree of particularity, it is understood that the present disclosure of the preferred form has been made only by way of example and that numerous changes can be resorted to without departing from the spirit and the scope of the invention.

We claim:

1. Method of converting acetone to isophorone and mesityl oxide which comprises contacting acetone vapor at a temperature of about 275° C. to about 350° C. and at a flow rate of about one volume of feed per volume of catalyst per hour with a heterogeneous catalyst prepared by (a) Introducing onto an alumina support a sufficient amount of an inorganic or organic calcium salt to provide a loading of from about 1 to 20 weight percent of calcium in the final catalyst whereby said alumina has a surface area in excess of about 30 meters$^2$/gram and an average pore volume in excess of about 0.40 cc/gram and (b) calcining the alumina supported calcium salt from step (a) at a temperature of about 300° to about 600° C. for at least about 3 hours; and recovering a product of unreacted acetone. isophorone and mesityl oxide.

2. Method claimed in claim 1 wherein the conversion is carried out in an inert atmosphere.

3. Method claimed in claim 1 wherein the conversion is carried out at a pressure of about 1–200 atmospheres.

4. Method claimed in claim 3 wherein the conversion is carried out at a pressure of about 1 to about 10 atmospheres.

5. Method claimed in claim 1 wherein the acetone is passed over the catalyst in the vapor form.

* * * * *